(12) United States Patent  
Gomez

(10) Patent No.: US 7,803,109 B2
(45) Date of Patent: Sep. 28, 2010

(54) METHOD AND APPARATUS FOR PROTECTING THE DISTAL LENS OF ENDOSCOPES

(76) Inventor: Ricardo Alexander Gomez, 571 Main St., Amherst, MA (US) 01002

( * ) Notice: Subject to any disclaimer, the term of this patent is extended or adjusted under 35 U.S.C. 154(b) by 1027 days.

(21) Appl. No.: 10/826,869

(22) Filed: Apr. 16, 2004

(65) Prior Publication Data

US 2005/0234295 A1 Oct. 20, 2005

(51) Int. Cl.
*A61B 1/04* (2006.01)
(52) U.S. Cl. .................. 600/121; 600/101; 600/133; 600/169; 126/263.04; 126/263.05; 126/263.06; 126/263.07; 126/263.08; 126/263.09
(58) Field of Classification Search ............. 600/101, 600/102, 133, 169; 206/363, 438
See application file for complete search history.

(56) References Cited

U.S. PATENT DOCUMENTS

| | | | | | |
|---|---|---|---|---|---|
| 4,256,225 | A | * | 3/1981 | Jackson | 206/303 |
| 4,730,729 | A | * | 3/1988 | Monch | 206/370 |
| 5,314,070 | A | * | 5/1994 | Ciarlei | 206/570 |
| 5,323,899 | A | * | 6/1994 | Strom et al. | 206/363 |
| 5,351,675 | A | * | 10/1994 | Brodsky | 600/169 |
| 5,400,767 | A | | 3/1995 | Murdoch | |
| 5,674,182 | A | | 10/1997 | Suzuki et al. | |
| 5,720,391 | A | * | 2/1998 | Dohm et al. | 206/438 |
| 5,784,195 | A | | 7/1998 | MacCollum | |
| 5,863,287 | A | | 1/1999 | Segawa | |
| 5,910,106 | A | * | 6/1999 | Morgan et al. | 600/169 |
| 6,066,089 | A | * | 5/2000 | Costello et al. | 600/102 |
| 6,142,636 | A | | 11/2000 | Nemoto et al. | |
| 6,527,115 | B2 | * | 3/2003 | Rabiner et al. | 206/363 |
| 6,574,431 | B2 | | 6/2003 | Mikami et al. | |
| 6,749,063 | B2 | * | 6/2004 | Parker | 206/363 |
| 6,846,285 | B2 | * | 1/2005 | Hasegawa et al. | 600/102 |
| 6,910,582 | B2 | * | 6/2005 | Lantz | 206/593 |
| 2002/0022762 | A1 | * | 2/2002 | Beane et al. | 600/101 |
| 2004/0188302 | A1 | * | 9/2004 | Rogers, Jr. | 206/438 |

* cited by examiner

*Primary Examiner*—Matthew J Kasztejna
(74) *Attorney, Agent, or Firm*—McCormick, Paulding & Huber LLP

(57) ABSTRACT

An apparatus which is self-contained, disposable, utilized for protecting the distal lens of endoscopes. The apparatus is sterile and is used as a holder or as an anti-fog solution applicator for the scope while protecting it from impact with a shock absorbent outer housing. A new method for protecting endoscopes by placing an inexpensive sterile protective cover over the distal lens of the endoscope which entails, placing the protector over the distal lens prior to medical procedure, protective cover is used intermittently and repeatedly during the medical procedure when the scope is not in use. Finally, at the end of the medical procedure the protective cover is placed over the distal lens and not removed until the scope reaches the area where it will be cleaned and sterilized. By protecting the scope prior to, during and after a medical procedure, endoscope repairs are reduced thereby saving hospitals money.

1 Claim, 5 Drawing Sheets

METHOD AND APPARATUS FOR PROTECTING THE DISTAL LENS OF ENDOSCOPES

FIELD OF INVENTION

This invention relates to the apparatus and the method for protecting the distal lens of endoscopic instruments prior to, during, and after medical procedures. More specifically to a sterile apparatus and procedure for protecting the distal lens of laparoscopes, arthroscopes, bronchoscopes, colonoscopes and all such telescopic devices used in endoscopic medical procedures.

BACKGROUND

The word endoscopy is derived from the Greek words. "Endo" meaning "inside" and "skopeein" meaning "to see". This is the word used in medicine to describe, in general, viewing the inside of the body. In medicine, to see inside the body is made possible by the use of different special fiber optic scopes. Fiber optic scopes are like telescopes. They are slender and contain several lenses. One lens at the very distal end of scope, which is inserted inside the body, and another lens in the most proximal part of the scope. The distal lens is also surrounded by delicate light emitting fibers that are used to light up the space around the lens inside the body. Depending on the body region that the endoscope is used in, the shape and size of the scope will vary. The name of the scope also depends on the body part that it is used. Arthroscopes are the type of endoscopes used to view the inside of human joints. They are very short rigid and thin. The distal lens of an arthroscope is very small and extremely delicate. Colonoscopes are the scopes used for viewing inside the large intestine "colon" These scopes are long and have a large lens at the distal end. Still, all endoscopes have at least two things in common. First, they all have a distal lens, the only lens that is inserted inside body so it must be as slender as possible therefore it is not covered by any thick metal or permanent cover. Second, repairing endoscopes scratched or cracked distal lens is very costly. Additionally, damaged scopes are often discovered at the beginning of a procedure and many times replacements are not quickly available. The broken equipment creates an incalculable cost from anesthesia, hospital room and all other expenses related to delaying medical procedures. It is estimated that collectively hospitals spend 6-10 million dollars per year in endoscope repairs. Again, this is not counting the enormous indirect costs that result from delays caused by the damaged scopes. The delays caused by damaged scopes are not only expensive but also dangerous. When medical procedures are delayed due to a damaged scope and time is wasted looking for a replacement, sterile replacements aren't usually quickly available; the patient is unnecessarily kept under anesthesia for a longer period of time, which is always a very dangerous risk.

Prior art has described many devices to protect the entire scope; some prior art has also described small apparatuses to protect the distal end of endoscopes. All of these methods and apparatuses are not completely efficient and all suffer from similar problems. The protectors that have been designed to protect the entire scope fall short in that they are too large and bulky, making them inconvenient to have easily and quickly available. Also, these protectors can only be used when transferring the scope to the medical procedure from storage and after the procedure from the medical procedure room back to the sterilizing center. The initial problem with many of the protectors is that they are not sterile and so are not able to be used during the majority of procedures. Even the protectors that are sterilized, they are not designed to be used during the medical procedure. Since these protectors are bulky and take up a lot of room, the nurse always removes the scope from the protector while setting up the instrument table. In addition, none of these protectors are designed to be used during the intermittent times that the scope is not inserted inside the body. For example, during a laparoscopic removal of the gall bladder, the scope is always removed intermittently during the case, at least once during the extraction of the organ from the body after resection, sometimes again while doctors are stitching the first entrance ports. Sometimes, cases start as an endoscopy but then turn into an open operation and the scopes are removed from the body for the rest of the case. Scopes in these situations are very vulnerable to damage from other instruments and instrument trays. The biggest problem with the prior art describing distal protectors is again the fact that they are not sterile or designed to be used immediately prior or during the medical procedure. Also, even the sterile distal protectors are not completely effective in protecting damage to the distal lens. Their thin tight design covers the distal lens and protects against scratches to the lens but they do an inadequate job in protecting the distal scope from shock that could crack the lens or rupture the delicate fiber optic fibers. Since the protectors are thin and the outer walls are in direct contact with the distal portion of the scope, any shock or trauma to the protector is directly transferred to the distal scope. To protect from shock the distal end of the endoscope must be separated by a space from the protective wall so that the wall only absorbs the energy and it is not transferred to the lens. No prior art has described a sterile method and an apparatus to protect the distal lens of endoscopes from shock and from scratches immediately prior to and during a medical procedure as well as after the procedure is complete

SUMMARY OF THE INVENTION

The present invention is a new and unique method and apparatus for protecting endoscopes and reducing the cost of endoscopic repairs for hospitals. The present invention entails a small, inexpensive, sterile, disposable device that covers the distal end of endoscopes. This device consists of an outer housing (2), which is constructed of a shock absorbing material. In the center of the device is a central sheath (6), which can accommodate the distal portion of an endoscope. The device can be constructed with specific sized openings and sheaths (6) so as to accommodate any diameter scopes. The central sheath (6) is separated from the wall of the outer housing (2) by a space. This space is essential in preventing the transfer of energy from the outer protective shell to the distal scope within the central sheath (6) therefore protecting the distal lens from shock and scratches. The present invention also presents a new and unique method for protecting scopes. This procedure entails the described apparatus to be aseptically opened during the instrument setup prior to the endoscopic procedure. Once the endoscope is opened or placed into the instrument and supply table the protective device is immediately placed over the distal end of scope. The nurse can then continue to prepare and set up for the procedure. Once the doctor is gloved and gowned and the patient is prepped and ready the scope containing the distal protective device over the distal portion are brought up to the operative field together. Only immediately before the scope is inserted into the body does the doctor remove the protective device from the distal portion of scope. The protective device can be clamped or stuck with an adhesive on to the drapes within reach of the doctor. Each and every time that the scope is removed from the body and not in use, the distal lens is inserted inside the protector and the scope is rested down. Upon the completion of the procedure the protective device is again placed and maintained over the distal portion of scope during closure and clean up of procedure. After clean up, the protective device is left remaining during the transfer of the scope from the procedure room to the sterilizing room. It is only finally removed immediately prior to the scope being cleaned or sterilized. Using this inexpensive, disposable device and following the method of use, hospitals can potentially save thousands if not millions of dollars in repair costs. Not to mention the incalculable costs associated with the delays caused by damaged scopes. This device and method will also help prevent infections caused by contaminated scopes. Since this device is also a sterile cover for the distal end of the scope. Even if the entire scope becomes contaminated prior to or during the procedure, the sterile protective device will prevent contamination of the distal lens and maintain it free of bacteria. This is significant since the only portion of the scope that comes in direct contact with the inside of the body is the distal end. Additionally, the interior of the protective device can contain anti-fog solution. This device would then not only protect the scope from damage but also protect the lens from fogging during medical endoscopic procedures, allowing the doctor to perform the procedure faster and with better visualization.

BRIEF DESCRIPTION OF THE SEVERAL VIEWS OF THE DRAWING

These objects and features of the invention will be more clearly understood from the following detailed description along with the accompanying drawing figures, wherein.

DETAILED DESCRIPTION OF THE INVENTION

Figure 2:
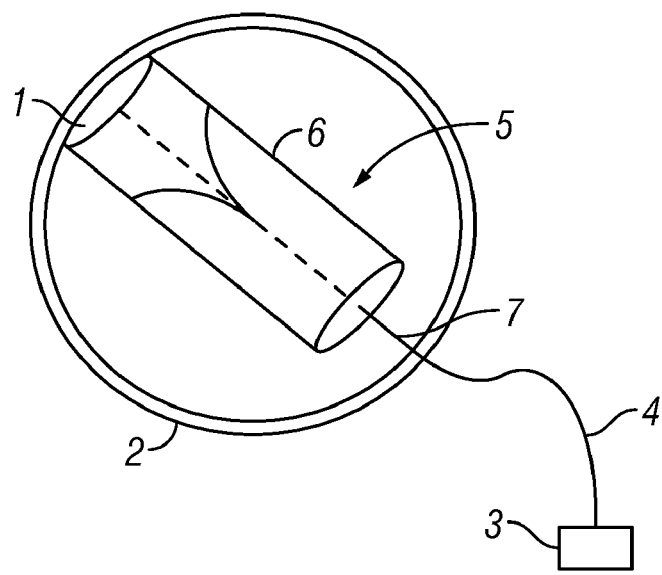
FIG. 2. A view of the interior components of the apparatus

As shown in FIG. 2, one particular embodiment the apparatus described in this invention comprises of an outer housing (2) made of a foam material or any solid yet shock absorbing insulating material. This shell is designed to protect the lens of the scope or any other type of instrument from damage prior, during, and after the procedure. The material has to also be inexpensive since the apparatus is disposable and for single patient use. The outer housing (2) cover is preferably constructed of any high density Polyurethane, Etha, Viscoelastic, Latex foams, or the like. It can also be made from rubber foam. A Semi-flexible thermoplastic can also be used. The outer housing (2) can also be made from Insulating cardboard or a thick insulating fabric. The outer housing (2) can alternatively be constructed out of a plastic frame covered by a silicone rubber or insulating plastic. It is important that the material have good shock absorbing and insulating properties. Alternatively, a cavity may be formed between the outer housing and the storage sheath (6) which can be filled with an impact absorbing and/or dampening material such as but not limited to: liquid, gel, gas, or Styrofoam.

Figure 1:
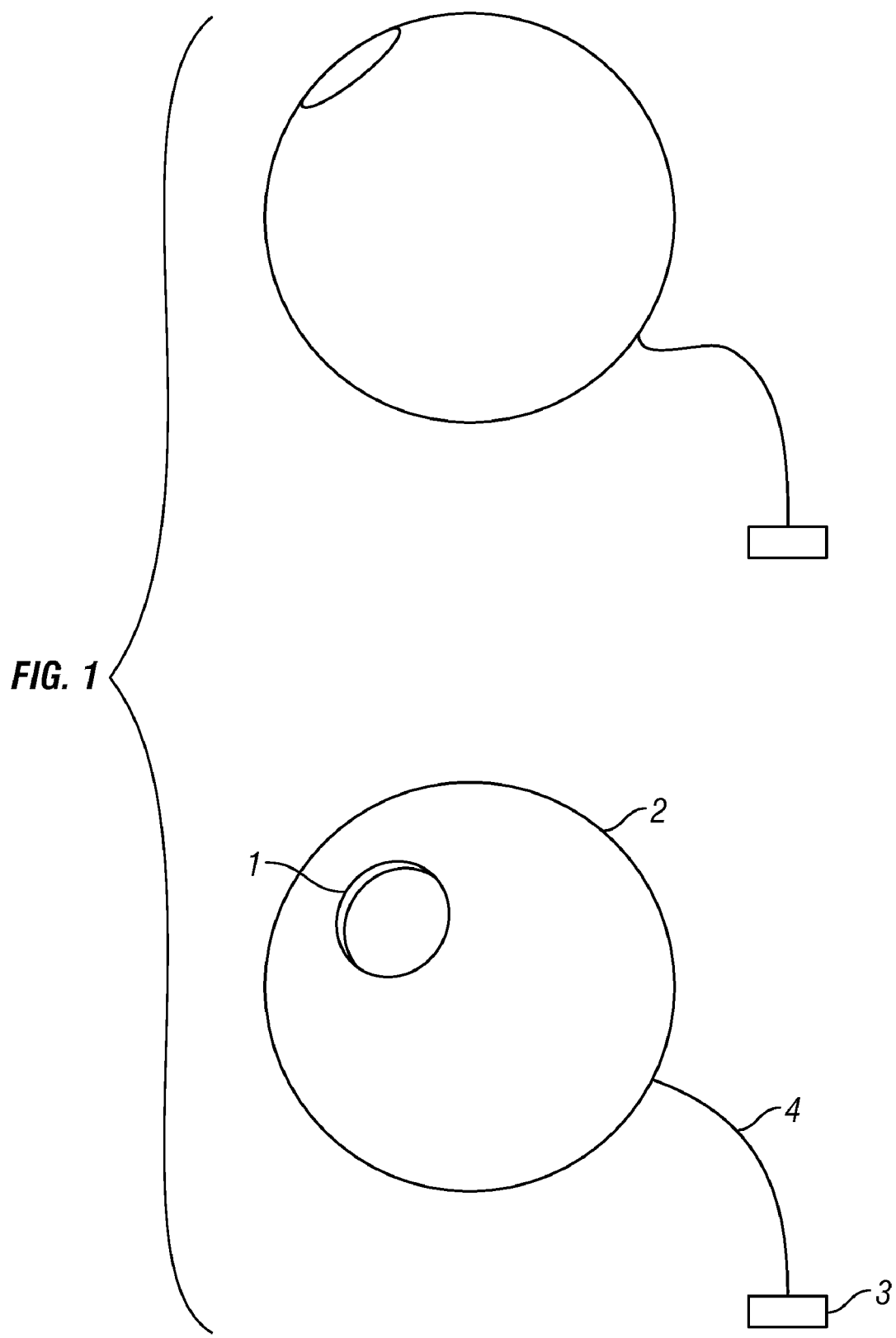
FIG. 1. A side and angled view of the exterior of apparatus
Figure 6:
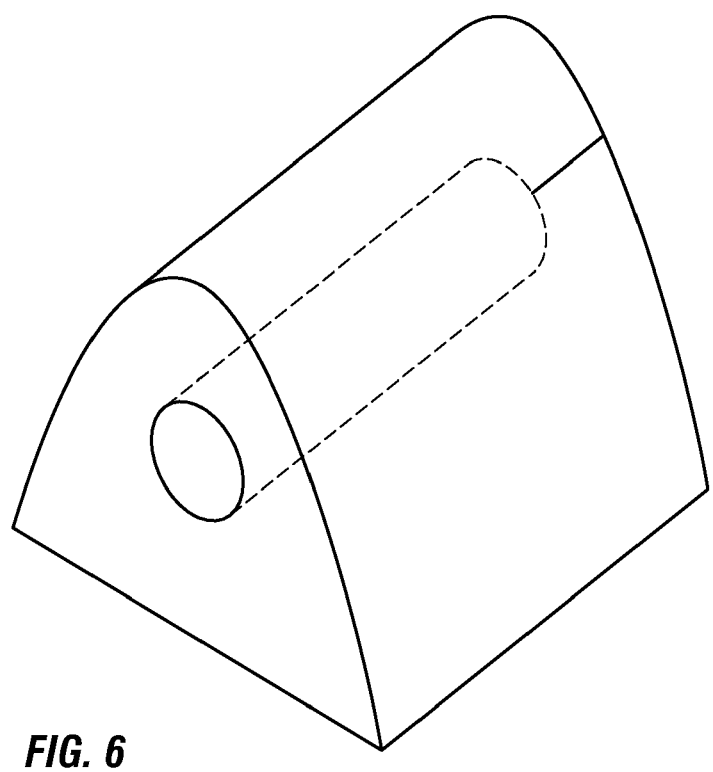
FIG. 6. Alternative outer shape for endoscope protector.
Figure 7:
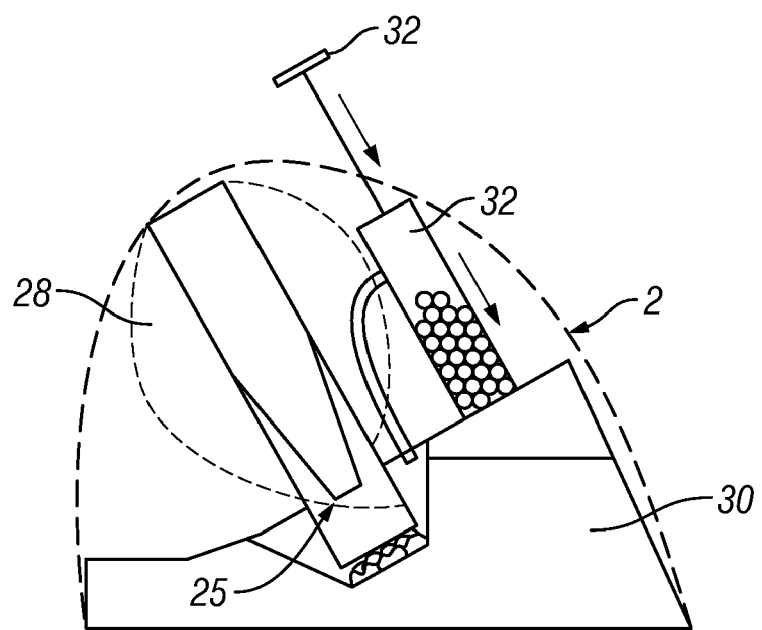
FIG. 7. A side view showing the internal components of the apparatus of FIG. 6.
Figure 8:
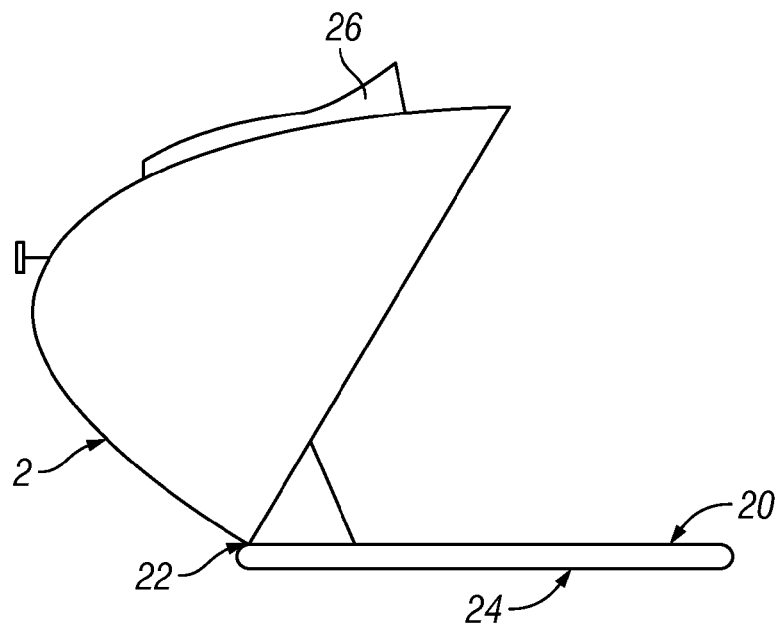
FIG. 8. A side view of the apparatus of FIG. 6 showing a flap mechanism.
Figure 9:
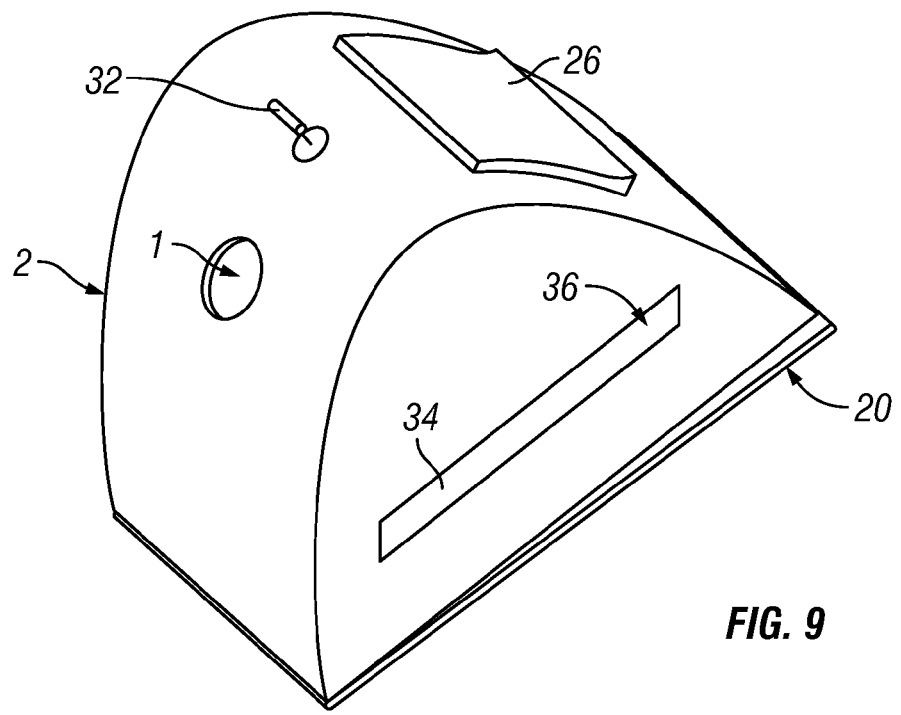
FIG. 9. A rear perspective view of the apparatus of FIG. 6.

The outer housing (2) is preferably in a spherical shape as in FIG. 1 but can alternatively be made in any shape; square or spherical, clearly shown in FIG. 6. The apparatus can also have a tubular shape. The apparatus can have rounded corners or square corner. The entire apparatus exteriorly is preferably 4 inches long, 3.5 inches wide, and 4 inches high but can be as small as 2 inches wide and 2 inches long and 2 inches high. Alternatively the apparatus can be as large as 6 inches wide, 6 inches long and 8 inches high. Clearly, the apparatus can be sized to conform the shape of any instrument used. The endoscope is inserted into the apparatus through an opening (1) on the outer housing.

Figure 3:
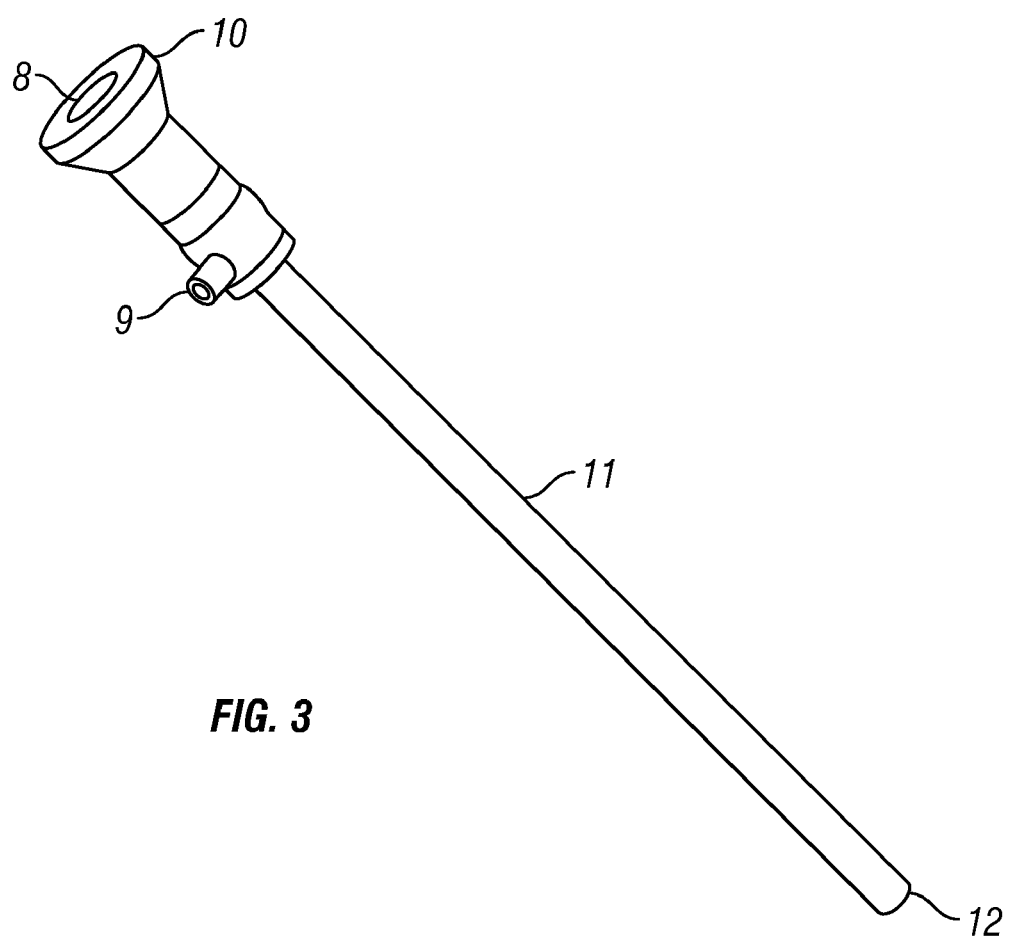
FIG. 3. Drawing of a laparoscope which is a type of endoscope and a description of some of its components.
Figure 4:
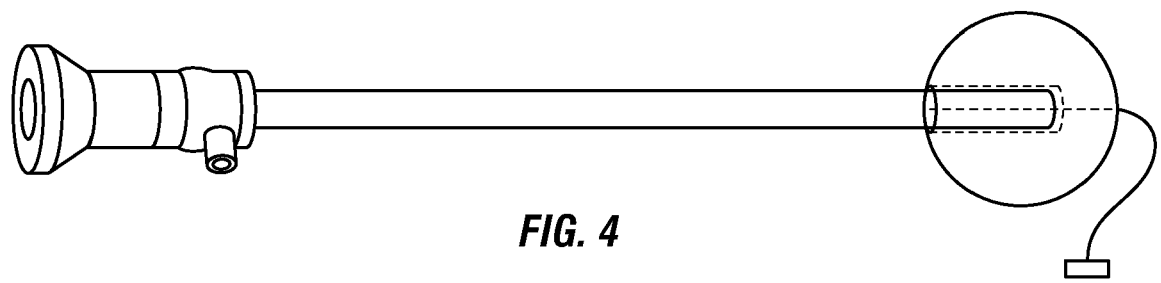
FIG. 4. Apparatus placed over endoscopes to demonstrate size relationship.
Figure 5:
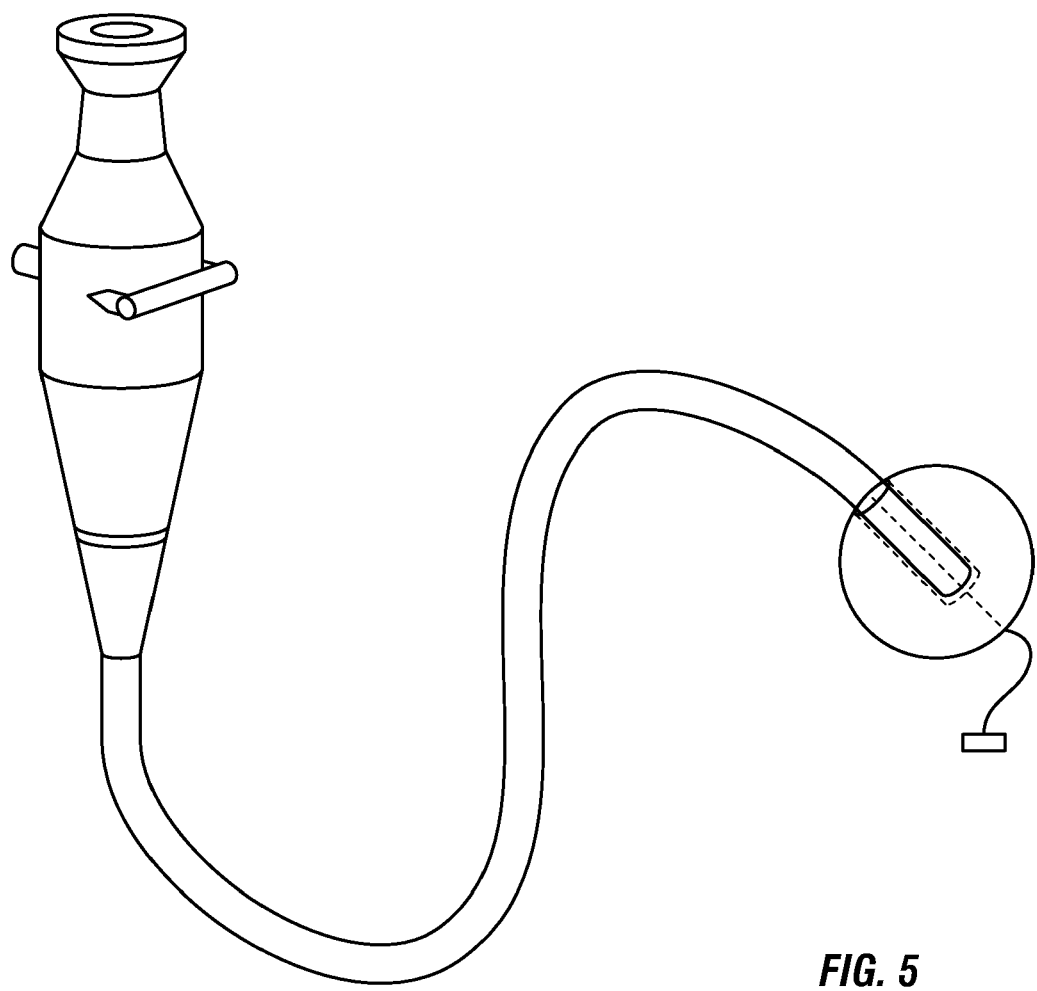
FIG. 5. Alternative type of endoscope.

A common type of endoscope which can be utilized with this apparatus is shown in FIG. 3: viewing proximal lens of Laparoscope where video attaches (8), connector for attaching the light source (9), solid cover built into scope to protect and allow for video attachment to the proximal lens (10), shaft portion of laparoscope (11) and distal lens of laparoscope (12). The apparatus is intended to protect the distal lens (12) by inserting the shaft of the laparoscope (11) into the apparatus as shown in FIG. 4. FIG. 5 shows an alternate type of endoscope with a flexible shaft (11). Any type of endoscope known to persons skilled in the art may be utilized with this apparatus.

The apparatus can be affixed to any surface by any means known to persons skilled in the art, such as, but not limited to adhesive, screw, magnetism, VELCRO, mount, clip, or fastener. Alternatively, the apparatus can be secured to a cord (4) which in turn attached to an anchor (3). The anchor can be affixed to any surface by any means known to persons skilled in the art, such as, but not limited to adhesive, screw, magnetism, VELCRO, mount, clip, or fastener. The anchor or the apparatus may be capable of being removed once use of the apparatus is completed. Alternatively the storage sheath may be fixed into position by at least one mooring (7).

In an alternative embodiment, the bottom of the outer housing (2) contains solid flap (20), which can have the same perimeter as the base of the outer housing (2). This flap is attached only at the front bottom part of the apparatus creating a hinge (22). The flap is also attached in the middle by two elastic bands. The flap can be constructed of a high-density foam material, cardboard or plastic. The external face of the bottom flap has an adhesive material that has a protective cover (24) until it is needed. When the surgery begins and the surgeon brings the apparatus up to the operative field he can secure the apparatus anywhere on top of the drapes by removing the protective cover from adhesive bottom and sticking the apparatus anywhere on the operative filed. The function of the flap is so that the scope can be inserted vertically but when it is not in use, is the flap mechanism allows the apparatus to rotate horizontally while the scope remains inside the apparatus. Although the apparatus rotates along the hinge, the flap maintains it securely attached to the drapes by the adhesive flap. Alternatively, the apparatus may be constructed without the flap and the adhesive can be placed directly on the bottom of the apparatus. Also the apparatus can be secured on any surface through such devices as but not limited to: adhesives, screws, magnetism, mounts, clips, or VELCRO.

Alternatively, the exterior of the apparatus may contain a soft, non-scratch, absorbent sponge (26) in the uppermost part. The sponge can be square in shape or in the shape of a rectangle. Alternatively the sponge can be in the shape of an eclipse or a circle. The sponge can be ¼ to {fraction (1/16)} of an inch thick. This sponge is used to wipe the excess defogging solution from the scope after it is removed from the apparatus and can also help with cleaning blood from the scope when it is removed from body cavity.

Internally the apparatus contains a center sheath (6) (2). This center sheath (6) has a center canal that accommodates the scope. This sheath (6) preferably runs directly down the center or the apparatus from the upper front to the lower back. The sheath (6) can alternatively run directly down the center or lateral to the center. The location of the sheath (6) can be in any configuration as long as uniform thermal conductivity is achieved. The length of the sheath (6) is preferably 3 inches long but can be as long as 8 inches. The sheath (6) has the shape of a tube but can also be constructed of two flat pieces attached together in the upper and lower thirds leaving a tubular canal in the middle. The tubular space inside the sheath (6) can be 5 mm or up to 10 mm, or any length depending on the instrument intended to be used. One embodiment of the sheath (6) is preferably constructed of but not limited to a thin piece of high-density Polyurethane, Etha, Viscoelastic or Latex foams. It can also be made of rubber foam or thin plastic. A water impermeable fabric can also be use. The sheath (6) can alternatively be constructed of silicone or rubber.

An alternative embodiment most distal or innermost part of the center sheath (6) (2) penetrates a reservoir. This reservoir can be constructed of the same material as the sheath (6) but is preferably made from a metal or any good heat conducting metal such as iron, aluminum, steel, and copper. The reservoir itself can also be made of a magnetic metal material. The reservoir can be in the shape of a box or a cylinder. It can be anywhere from ½ an inch to 2 inches long and wide enough to accommodate at least a 5 mm to 10 mm scope and still allow some space around the scope. The reservoir is preferably filled with a defogging solution. The defogging solution can be made of a combination of water, glycol, and a water-soluble wetting agent but not limited to such. Alternatively, the defogging solution used can be any commercially available surgical defogging solution such as F.R.E.D™. The reservoir can also be filled with only plain water or saline. Ideally any chemical able to enhance or facilitate the use of an instrument may be used.

Internally, inside the canal between the reservoir filled with defogging solution and the central sheath (6) is a valve mechanism. The valve mechanism is preferably constructed by enclosing the reservoir around the distal aspect of the sheath (6) while at least 1 inch overhangs . . . . The valve mechanism preferably resembles a tube within a tube. The tube within a tube mechanism that allows for the scope to enter the reservoir and make contact with the solution but prevents any fluid from spilling out of the reservoir when the apparatus is turned upside down with the scope removed. The way it liquid is prevented from falling out functions by creating a pocket around the distil end of the sheath (6). When the sheath (6) is turned with the reservoir down all the liquid will fall into the reservoir. As the sheath (6) and reservoir are turned upside down, the liquid slides along the side and enters the pocket surrounding the distal sheath (6). Alternatively, the valve mechanism can also resemble a heart valve or be made with a flap and a hinge that only opens in one direction. The valve can also resemble a valve in a human vein. The valve can be a ball and socket mechanism in which a ball inside the reservoir plugs the hole when the reservoir is turned upside down but still allows for the scope to enter in the other direction. The valve mechanism can be constructed from a plastic material. It can also be made from the same material used for the sheath (6) such as a high-density foam or water impermeable fabric. The valve can also be made of metal, aluminum, or silicone. The valve (25) can be any self sealing mechanism known to person skilled in the art to prevent leakage and splash black of fluid.

The entire center sheath (6) including the distal reservoir segment is surrounded by compound, that is unoxidized but can become easily oxidized and release heat energy when it is oxidized. Oxidation reactions are always exothermic, meaning that they always release heat. Metal compounds share the common characteristic that when in their elemental form they are prone to donate electrons and are easily oxidized. The metal preferably used to surround the sheath (6) would be Iron or Fe. The iron is preferably in powder form but can be in pellets or as shavings garnering a large reactive surface area. The Iron used is preferably a commercially available mixture, which uses a combination or Iron, vercumilite, activated charcoal, and water. This commercially available mixture from (mycoal) or (heatmax) can provide up to 6 hours of heat when the iron is oxidized by atmospheric oxygen. Other metals such as Mg, Aluminum, Nickel or Copper can also be used. Unoxidized Non-metals can also be used in gas, powder, or liquid form. The material is preferably in an oxygen permeable membrane wrapped around the sheath (6). The amount of material surrounding the sheath (6) can as thin as ⅛ of an inch to as thick as to fill the entire upper chamber. The unoxidized material can also be in liquid form surrounding the sheath (6) and reservoir. It can also be in a bag surrounding the sheath (6) and reservoir. The bag can be made of plastic or impermeable rubber foam. Any combination of reactants known to persons skilled in the art can be utilized to create the exothermic reaction.

The one embodiment for heating the defogging solution inside the reservoir as well as the long lasting sustained heating of the apparatus uses three separate exothermic reactions The first reaction uses the energy generated from a fast exothermic decomposition of Hydrogen Peroxide to heat the reservoir very quickly. The second reaction is a slower but consistent decomposition of $H_2O_2$. The third reaction uses the oxygen molecules generated in the first and second reaction to slowly oxidize the iron material surrounding the upper part of the reservoir and the central sheath (6) and heat the apparatus for a longer sustained period of time.

Hydrogen peroxide ($H_2O_2$) is an unstable molecule, which quickly and spontaneously decomposes to $H_2O$ (water) and $O_2$ (oxygen gas). The balanced equation of the reaction is $H_2O_2+H_2O_2=2H_2O+O_2$. This decomposition reaction is very exothermic. Although $H_2O_2$ decomposes spontaneously the rate is much to slow at room temperature. A catalyst is a molecule that facilitates and speeds up the rate of a given reaction. When a catalyst is added to $H_2O_2$ the decomposition of $H_2O_2$ speeds up greatly causing the $H_2O_2$ solution to heat up a large quantities of Oxygen gas are released. By controlling the amount of catalyst one can control the amount of Oxygen gas generated and the amount of heat released to the solution. In the preferred mechanism the catalyst used is Iron oxide. Alternatively the catalyst can be any molecule that speeds up the decomposition of $H_2O_2$. Alternatively catalysts such as manganese dioxide, manganese (IV) oxide, silver catalyst, and potassium permanganate can also be used. The natural enzyme, catalaze that is designed to decompose $H_2O_2$ in plants and yeast can also be used. The catalyst is preferably in powdered form or in pellets. It can also be in shavings, crystals, and salt or in liquid form. The Shape and type of catalyst determines the precise rate of $H_2O_2$ decomposition. The Powdered form of catalyst is much more reactive than the pellet form because of the larger surface area.

An alternative embodiment entails a mechanism for activation and function of the preferred heating method. This method accomplishes two things. Upon activation, a fast reaction occurs and the solution in the reservoir is almost immediately heated above body temperature, the heated solution is then maintained above body temperature along with the interior of the apparatus for up to 7 hours.

An alternative embodiment contains all the components for an embodiment of the exothermic reaction. The interior of the apparatus comprises two chambers. One upper chamber (28), which contains the unoxidized material surrounding the sheath (6) and a lower H2O2 containing chamber (30). The H2O2 is contained in a thermo plastic container. The container can alternatively by made from aluminum, copper, iron or any material suitable commonly known to persons skilled in the art. The H2O2 can also be kept in high-density Polyurethane, Etha, Viscoelastic or Latex foam or rubber foam container or any non reactive materials. The H2O2 could also be maintained in a heat resistant plastic or silicone bag. The H2O2 is preferably maintained in the lower part of the apparatus. Alternatively the H2O2 can also be stored in the back or upper part of apparatus. The H2O2 can also be maintained in a container outside the apparatus.

The H2O2 is stored in one embodiment, in a plastic chamber that also contains a cup shaped indentation, vacuole at the top part of the container. The indentation creates a space, which surrounds the reservoir. Inside the space surrounding the reservoir there is a small amount of powdered iron oxide catalysts. This catalyst is found between the reservoir and the internal floor of the cup shaped indentation. The indentation is at least large and deep enough to fit the reservoir and the surrounding unoxidized material. The indented cup exterior is inside the bottom chamber and is surrounded by H2O2 since it penetrates any where from ½ inch to three inches inside the H2O2 container. The external bottom of the cup shaped indentation contains a magnet. The indentation in the H2O2 filled container can be any shape as to allow the reservoir bottom and sides to be in direct contact with the H2O2, only separated by the plastic or material that makes up the wall of the H2O2 filled chamber. The cup shaped indentation can alternatively be devoid of a magnet. Alternatively the H2O2 can be completely separate without any indentation, and the reservoir can just sit above the H2O2 receptacle. In this specific mechanism, the H2O2 filled container has a hole in the uppermost part of the chamber. This hole is sealed by a thin film. Sitting directly above the film-covered hole in the upper chamber, is a cylinder or hollow tubular container with one open end directly making contact with the film seal covering the hole. Preferably the hollow cylinder is made from plastic. The seal can also be constructed of aluminum, metal, ceramic, or any other suitable material known to persons skilled in the art. The film sealing the hole in the H2O2 filled container can be constructed of a thin plastic or aluminum paper or a thin water impermeable paper or fabric. Alternatively a one-way valve that is normally closed but can be opened when the plunger cylinder (32) pushes through can also be used to create the seal. The tubular hollow container sitting directly above the film-covered hole is filled with the iron oxide catalyst. The iron oxide catalyst is preferably in shavings or small pellets the amount and shape of the catalyst controls the rate in which the decomposition of H2O2 occurs thereby controlling the generation of heat and oxygen. The Film covered hole on the upper wall of the H2O2 container is at least as wide as to allow the catalyst filled cylinder to slide trough. The uppermost part of the cylinder is closed ended and has a solid extension to the exterior of the apparatus. The extension can be a small plastic rod. Alternatively it can be a wooden, metal or aluminum rod. This extension has a flat part in the exterior of the apparatus. Alternatively, the cylinder can be made without a plunger extension and the cylinder itself can be long enough to penetrate to the exterior of the apparatus. Any method commonly known to persons skilled in the art can be utilized to initiate the exothermic reaction.

In the upper part of the catalyst filled cylinder is a small tube. This tube is open on both ends. One open end is inside the catalyst filled cylinder and the other open end is inside the cup shaped indented space surrounding the reservoir. The tube creates an open communication between the inside of the catalyst filled cylinder and the space containing powdered catalyst surrounding the reservoir. The tube is preferably constructed out of flexible plastic, or rubber. Silicone, PVC, copper or aluminum tubing can also be used but is not limited to such.

An alternative embodiment may include the first step of the activation of the exothermic reaction. When activation is desired, downward pressure is applied to the external flat part of the extension of the catalyst-containing cylinder. Once the downward pressure is sufficient enough, the catalyst-containing cylinder will break through the film or seal separating the lower chamber the catalyst-containing cylinder will then enter the lower H2O2 containing chamber. The cylinder is pushed about an inch deep into the H2O2 solution. Once the cylinder breaks the seal gravity will cause the Iron oxide pellets to fall out of the cylinder and enter the H2O2 solution. The H2O2 solution then begins to slowly decompose at a controlled speed that is dependant on the quantity and shape of the catalyst. As soon as the iron oxide catalyst fall out of the cylinder and enter the H2O2 solution the iron oxide pellets are attracted to the magnet located in the external bottom of the cup shaped indentation. This causes all of the catalyst to congregate around the magnet. By having all of the catalyst congregate around the magnet, the H2O2 decomposition will only occur around the external aspect of the cup shaped indentation. The heat generated from the decomposition is therefore much more efficiently transferred to the space around the reservoir allowing for faster heating of the defogging solution in the reservoir. Alternatively the catalyst can also be introduced by having a double close ended, thin walled glass tube filled with the catalyst. When desired, the glass tube is broken and the catalyst is consequently introduced to the H2O2. Another method is to use a liquid catalyst and maintain it in a container or bag above or adjacent to the H2O2. When desired, a seal dividing the liquid catalyst and the H2O2 can be broken and the liquid catalyst is allowed drip into the H2O2. The rate of the decomposition and the amount of O2 generated can then be controlled by the rate and amount of the catalyst drip. Once the catalyst is introduced to the H2O2 chamber, the H2O2 begins to decompose at any predetermined rate.

As shown in Figure 13 the H2O2 begins to decompose into H2O and O2 gas the gas rises up to the top of the H2O2 containing chamber. (Figure 14) shows the O2 gas building up in the top part of the H2O2 containing chamber. As more and more O2 is generated the pressure begins to rise. The pressure of the O2 gas pushes on the liquid and the H2O2 surrounding the cylinder begins to be pushed inside the cylinder. As the O2 pressure continues to raise even more the H2O2 that entered the cylinder is pushed in further. The H2O2 enters the small tube and then flows out of the distal end of the tube and into the interior of the indented cup shaped space. Since the H2O2 that enters the space around the reservoir is a small amount and the powdered iron oxide catalyst has a large surface area, the H2O2 decomposes vigorously when it makes contact with the powdered iron catalyst. Large amounts of heat are quickly released and transferred to the reservoir. Since this reaction occurs in direct contact with the reservoir containing defogging solution the solution inside the reservoir is virtually instantaneously heated. At the same time a bolus of Oxygen gas is generated inside the space from the fast decomposition reaction. This Oxygen gas quickly rises into the upper chamber and begins to exothermically oxidize the Iron Material thereby heating the sheath (6) and upper part of the reservoir. The O2 gas continues to be generated in the lower chamber increasing the pressure even more. The Oxygen gas travels into the empty cylinder and then into the tube pushing out all the remaining H2O2 into the space around the reservoir. After the ejection of the H2O2 into the indented space, the level of the H2O2 in the lower chamber becomes lower than the opening of the cylinder, H2O2 cannot enter the cylinder anymore, and only the O2 gas generated passes into the cylinder. Once all of the H2O2 has completely entered the indented cup shaped space. The O2 gas that is slowly generated in the lower compartment flows through the hollow cylinder and into the tube then out to the indented space where it quickly rises into the upper chamber. As the oxygen begins to fill the middle chamber, the unoxidized iron material begins to get oxidized by the O2 gas. This exothermic reaction is much slower than the decomposition reaction since the O2 is introduced slowly, and thus the heating can be sustained for a long period of time. As the material exothermically oxidizes, heat is generated and transferred to both the sheath (6) and reservoir, maintaining a sustained elevated temperature inside the apparatus. The interior of the apparatus and the solution inside the reservoir are maintained heated by both the heat generated by the H2O2 decomposition occurring in the lower chamber directly below the reservoir and also by the slow exothermic oxidation of the iron material in the upper chamber. The exothermic reaction can be sustained as long as desired by manipulating several factors. The quantity and concentration of the Hydrogen Peroxide, the rate of oxygen generation, which is determined by the speed of the decomposition reaction, and by the amount of, unoxidized iron material in the upper chamber. By generating the oxygen the apparatus can be self-contained and sealed completely from the environment as oppose to depending on atmospheric oxygen as the oxidizing agent. Also, by generating the oxidizing agent, one is able to control the amount and rate at which the oxygen is delivered, thus giving one control over the length of the exothermic reaction, speed of initiation, and the maximum temperature of the exothermic reaction.

The Oxygen molecule is preferably generated by the decomposition of 6% Hydrogen Peroxide but other concentrations below 30% will work. Alternatively, Oxygen can be generated from the decomposition of Potassium chlorate (KclO3). Also the oxygen can be generated from decomposition of oxides such as nitric oxide or Manganese dioxide. Oxygen molecules can also be generated by decomposition of salts such as Potassium nitrate. Oxygen can also be generated by the chemical decomposition of water or the electrolysis of water. The oxygen molecules can also come from atmospheric oxygen found in air.

The oxygen can be generated from the combination of two or more of the above methods. For example, some part of the oxygen can come from the decomposition of one of the mentioned chemicals and another part of the oxygen may come from atmospheric oxygen by way of a vent or opening in the exterior of the apparatus.

The heating of the apparatus and reservoir can alternatively be heated by using only atmospheric oxygen. The apparatus may contain small vents (34) in the exterior. These vents can be covered by a seal (36). When the seal is removed the interior is exposed to atmospheric oxygen, therefore oxidizing the material around the sheath (6) and reservoir heating the apparatus and the defogging solution in the reservoir The exothermic reaction can alternatively only contain two reactions. One is preferably a fast initial reaction that is used to quickly heat the reservoir containing defogging solution or saline. The second reaction is a slower sustained reaction that maintains the temperature within the apparatus above body temperature for a longer period of time.

The initial fast heating of the reservoir is preferably attained by the highly exothermic decomposition of H2O2. Alternatively the fast reaction can be generated from other chemicals such as Sodium acetate and water, Calcium chloride and water. Alternatively a battery and a heating filament can be used to heat the reservoir during the initial fast heating part of the dual reaction.

The second, slower, longer lasting reaction is preferably the oxidation of an iron mixture that contains Iron, vercumulite, water and activated charcoal. The sustained longer reaction can also be a combination of two chemicals located around the sheath (6). The chemicals can be H2O2, Calcium chloride and water or Sodium acetate and water. It can also be two chemicals that when combined form an exothermic reduction oxidation reaction. Alternatively, energy from a battery may also be used to heat the interior of the apparatus and maintain the temperature of the reservoir above body temperature for a sustained period of time.

A multiplicity of exothermic reactions may occur with a multiplicity of different reactants commonly known to persons skilled in the art.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. A sterile apparatus for protecting an endoscope comprising:
   a substantially triangular tubular impact resistant housing including:
      an outer surface defining an opening and vents;
      an interior of the housing defining a canal having a first end communicating with the opening and a second end terminating within the housing for receiving a distal lens of an endoscope, wherein defogging material is disposed adjacent to the second end of the canal for defogging a distal lens of an endoscope when inserted within the canal;
   a self-sealing mechanism disposed adjacent the first end of the canal and being configured to allow for an endoscope to enter the canal and make contact with the defogging material and to prevent the defogging material from spilling out of the canal;
   at least one first inner chamber abutting the second end of the canal and containing an unoxidized material selected from the group consisting of: iron, vercumilite, activate charcoal and water, wherein at least one of the at least one first inner chamber is in fluid communication with the vents;

at least one second inner chamber abutting the at least one first inner chamber with a penetrable thin film disposed therebetween and containing hydrogen peroxide; and at least one surface of the housing having a solid flap that is mounted to an end of the at least one triangular surface via a hinge-like connection, wherein at least one surface of the solid flap is coated by an adhesive; and wherein the impact resistant housing is constructed of a shock absorbing material;

a plunger cylinder mounted in the second inner chamber that is configured to penetrate the thin film between the at least one first inner chamber and the at least one second inner chamber;

a sponge mounted on the outer surface of the housing;

a removable vent cover disposed on the vents; and a removable protective cover disposed on the at least one surface of the solid flap that is coated by the adhesive.

* * * * *